United States Patent

Neftel et al.

[11] Patent Number: 6,085,574
[45] Date of Patent: Jul. 11, 2000

[54] DEVICE FOR CONTROLLING A LIQUID FLOW IN A TUBULAR DUCT AND PARTICULARLY IN A PERISTALTIC PUMP

[75] Inventors: Frédéric Neftel, Lausanne, Switzerland; Bernard Bouvier, Fragny, France

[73] Assignee: Debiotech S.A., Lausanne, Switzerland

[21] Appl. No.: 08/875,407

[22] PCT Filed: Jan. 5, 1996

[86] PCT No.: PCT/FR96/00019

§ 371 Date: Jul. 3, 1997

§ 102(e) Date: Jul. 3, 1997

[87] PCT Pub. No.: WO96/21151

PCT Pub. Date: Jul. 11, 1996

[30] Foreign Application Priority Data

Jan. 5, 1995 [FR] France ................................. 95 00053

[51] Int. Cl.[7] ................................................. G01N 29/02
[52] U.S. Cl. ................................ 73/19.03; 128/DIG. 13; 600/67
[58] Field of Search ................... 73/19.03; 128/DIG. 13; 600/438; 604/65, 67; 340/621

[56] References Cited

U.S. PATENT DOCUMENTS

| 4,487,601 | 12/1984 | Lindemann | 128/DIG. 13 |
| 5,123,275 | 6/1992 | Daoud et al. | 73/19.03 |

FOREIGN PATENT DOCUMENTS

| 0 053 453 A1 | 6/1982 | European Pat. Off. . |
| 0 181 272 | 5/1986 | European Pat. Off. . |
| 0 222 986 | 5/1987 | European Pat. Off. . |
| 0 419 094 A1 | 3/1991 | European Pat. Off. . |
| 0 495 538 A2 | 7/1992 | European Pat. Off. . |
| 0 643 301 A1 | 3/1995 | European Pat. Off. . |
| 91/16087 | 10/1991 | WIPO . |

*Primary Examiner*—John E. Chapman
*Attorney, Agent, or Firm*—Wolf, Greenfield & Sacks, P.C.

[57] ABSTRACT

A device for sensing gas bubbles in a liquid flowing through a duct, particularly the outlet duct of a peristaltic pump, including two piezoelectric components shaped and excited so that they vibrate axially. One of the components is a transmitter and the other is a receiver. One of the piezoelectric components is secured to a movable support, and its displacement is detected in order to detect excess pressure in the liquid flowing through the duct.

11 Claims, 3 Drawing Sheets

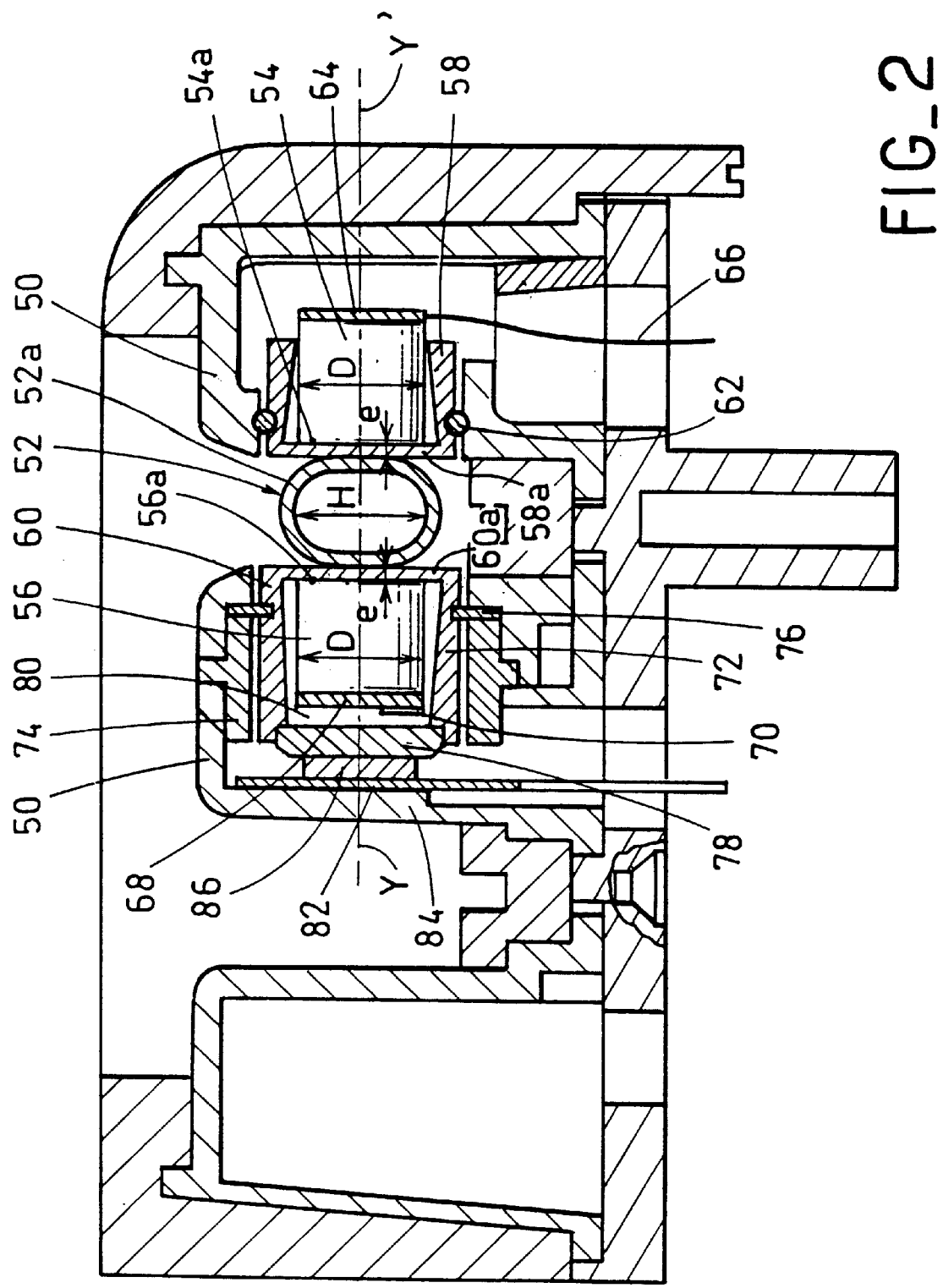
FIG_2

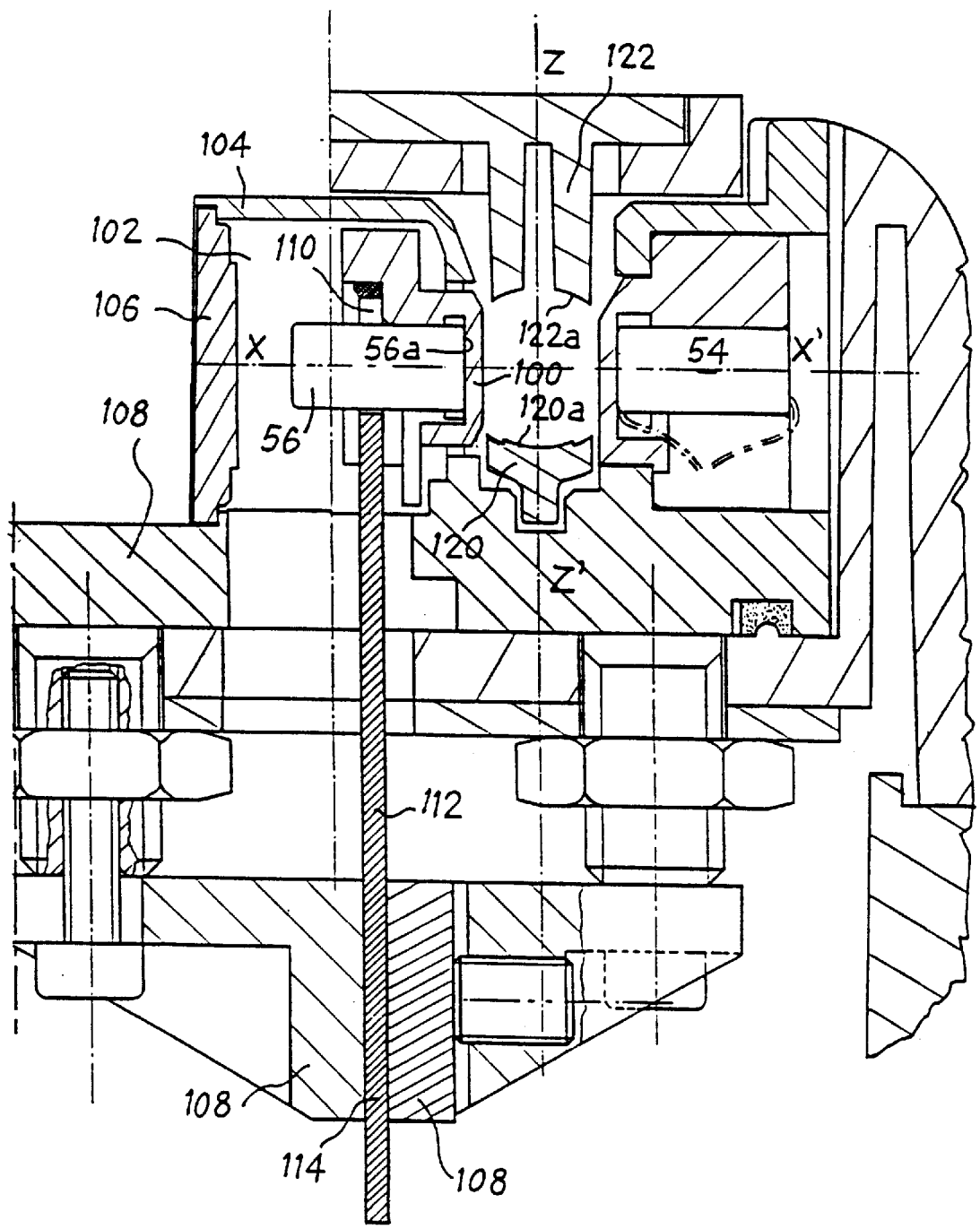
FIG_3

DEVICE FOR CONTROLLING A LIQUID FLOW IN A TUBULAR DUCT AND PARTICULARLY IN A PERISTALTIC PUMP

The present invention relates to a device for monitoring the flow of a liquid in a tubular duct.

More precisely, the monitoring device serves at least to detect the presence of bubbles of gas in the liquid flow, in particular when said tubular duct is the tube of a peristaltic pump.

There exist certain situations in which it is important to make sure that a liquid flowing in a duct does not accidentally entrain bubbles, and in particular air bubbles. This is particularly true of the medical field for ducts which serve to convey perfusion or other liquid for a patient.

In certain circumstances, the liquid is conveyed towards the perfusion needle in a duct, not merely under gravity, but with the help of a pump, e.g. a wheel or peristaltic pump. Such a pump is described, in particular, in French patent application No. 2 691 258 filed in the name of the Applicant. Such a disposition makes it possible to control more accurately the rate at which the liquid is injected. When using a pump, and regardless of the operating accuracy and leak-proofing it presents, it can always happen that there is an unacceptable quantity of air in the liquid, coming from an accidental insertion of air into the tank, from too great a quantity of air dissolved in the liquid, or possibly from an accidental cavitation effect causing bubbles of air to be entrained with the flowing liquid. It will naturally be understood that such a situation is completely unacceptable and that it is particularly important to be able to detect continuously any appearance of air bubbles in the duct, particularly at the outlet from the pump when such a device is designed to be able to interrupt the admission of the liquid.

In order to detect the possible presence of gas or air bubbles, proposals have already been made for optical detection systems. That is described, in particular, in the above-mentioned French patent application. Nevertheless, that optical detection can naturally only be used only when the liquid and the wall of the duct are translucent or substantially translucent.

To perform such detection, proposals have also been made to use ultrasound, given that it is known that the transmission coefficient or transmission impedance varies depending on the nature of the fluid, and thus varies depending on whether the liquid has no air bubbles or on the contrary includes air bubbles. In known ultrasound detection systems, a transmitter and a receiver are used which are constituted by piezoelectric cylinder disposed on either side of the tube, and the cylinders are excited in radial mode. That solution suffers from a first drawback which consists in the fact that, if the tube is placed in an environment that is itself liquid, the propagation of ultrasound due to the poorly-directional transmission from the piezoelectric cylinder is disturbed, thereby running the risk of allowing air bubbles to pass without being detected. Another drawback of such ultrasound transmitter/receiver devices is that, in order to obtain an ultrasound beam that is relatively directional, it is necessary to use relatively high excitation frequencies and consequently to perform detection on electric signals that are likewise at high frequency. Typically, these frequencies are greater than one megahertz and generally lying in the range 2 MHz and 5 MHz. As a result, the electrical and electronic environment of such detectors is relatively complex and thus expensive.

Advantageously, the present invention provides a device for monitoring the flow of a liquid in a duct, in particular for detecting bubbles of gas in the liquid. This device is very reliable while being of low cost and compact.

To achieve this aim, the device for monitoring the flow of a liquid in a tubular duct is characterized in that it comprises:

a support structure;

a first piezoelectric cylinder whose vibration axis is substantially orthogonal to said duct in the detection zone and which is mounted on said support structure to be disposed on a first side of said duct;

means for exciting said first piezoelectric cylinder in axial mode at a predetermined frequency F in order to transmit ultrasound waves;

a second piezoelectric cylinder whose axis coincides substantially with that of the first cylinder and mounted on said support structure so as to be disposed on a second side of said tube, whereby said second cylinder receives said ultrasound waves after they have passed through said duct;

means for picking up an electric signal representative of the amplitude of axial vibration of said second cylinder; and processor means for processing said electric signal to deduce therefrom the presence of a gas bubble, if any, in the liquid flowing in said duct through the detection zone.

It will be understood that by exciting the piezoelectric sensor in axial mode and by receiving the vibrations also in the axial excitation mode of the receiver, a highly directional ultrasound beam is obtained, and the excitation frequency F can lie in the range 100 kHz to 1500 kHz, depending on the nature of the piezoelectric cylinder, which frequency is very significantly lower than the previously known system. Consequently, the electric and electronic circuits can be considerably simplified.

Preferably, the support structure is the support structure of a peristaltic pump, and the tubular duct is the outlet portion of the deformable tube of said pump.

Preferably, in a plane perpendicular to the axis of the tube, the dimension of the transmitter/receiver face of the piezoelectric cylinder is no greater than the height of the bore of the tube.

Also preferably, the two piezoelectric cylinders are identical.

Also preferably, in the application of monitoring the liquid delivered by a pump of the peristaltic type, the monitoring device simultaneously includes means for detecting accidental excess pressure of the liquid in the outlet tube, said excess pressure causing the tube to be deformed.

This disposition is particularly advantageous since it makes it possible, if necessary, to stop operation of the pump in the event of difficulty in making the liquid flow, with such difficulty possibly being the result either of the tube being accidentally blocked, or else of difficulty at the perfusion needle.

Other characteristics and advantages of the present invention appear better on reading the following description of various embodiments of the invention given as non-limiting examples. The description refers to the accompanying figures, in which:

FIG. 2 is a vertical section view of a first embodiment of a device for detecting bubbles applied to the case of a peristaltic pump, the monitoring device further including means for detecting excess pressure in the tube; and FIG. 3 is a view analogous to FIG. 2 showing a second embodiment.

Figure 1A:
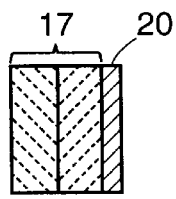
FIG. 1A is a partial cross-sectional view of a cylinder shown in FIG. 1.
Figure 1:
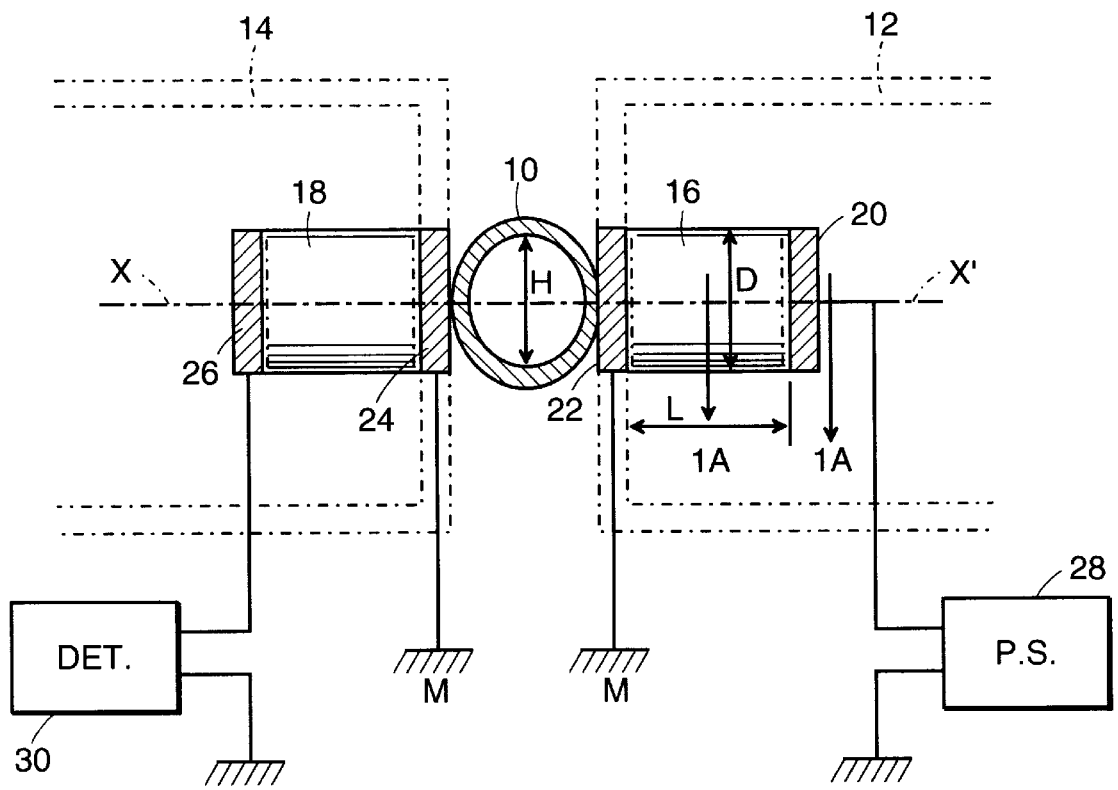
FIG. 1 is a simplified view of a device for detecting bubbles by ultrasound.

With reference initially to FIG. 1, an embodiment of the invention is described making it possible to detect the presence of gas bubbles, if any, in a liquid flowing in a duct.

In the figure, a tube 10 along which the liquid is flowing is shown in right section. The tube 10 is disposed in a support structure 12, 14 that is shown diagrammatically. Two piezoelectric cylinders given respective references 16 and 18 are mounted on the support structure 12, 14 on either side of the tube. The piezoelectric cylinders 16 and 18 are of the axial excitation type. They are generally cylindrical in shape having an actual length L that is greater than their diameter D. Electrodes 20 and 22 are formed at respective terminal ends of the transmitting cylinder 16, and electrodes 24 and 26 are formed at respective terminal ends of the receiving cylinder 18. The two piezoelectric cylinders substantially share a common axis XX' lying in the section plane of the duct 10 in the detection zone. In addition, the axis XX' is substantially orthogonal to the axis of the duct 10. The electrodes 20 and 22 are respectively connected to a frequency-controlled AC signal generator 28 and to ground M. It will be understood that by applying excitation electrical pulses at a predetermined frequency F, preferably corresponding to the natural frequency of the piezoelectric cylinder, to the electrodes 20 and 22 by means of the pulse generator 28, the cylinder is caused to transmit a directional ultrasound wave beam which passes through the duct 10 and thus through the liquid flowing therealong. The excitation frequency of the piezoelectric cylinder, when the cylinder is made of ceramics, preferably lies in the range 100 kHz to 1000 kHz; typically it is equal to 300 kHz. It will thus be understood that given its relatively low frequency, the pulse generator 28 and the associated electric circuits can be of relatively standard structure.

The cylinders 16 and 18 are preferably identical in order to optimize coupling.

Symmetrically, the receiving piezoelectric cylinder 18 converts its frequency of axial vibration into an electric signal at the same frequency F, which electric signal is picked up by a detector 30. Such detectors are known per se. They are preferably synchronous with the excitation frequency. By comparing the level of the received signal with predetermined thresholds, the detector can detect the presence of bubbles, if any, in the liquid flowing along the tube 10, because of a modification in acoustic impedance.

It should also be observed that given the excitation mode of the piezoelectric cylinders 16 and 18, the ultrasound beam is highly directional and measurement is not disturbed even if the detection device is itself in a liquid medium.

In order to obtain optimal detection of bubbles in the tube 10, in the plane of the figure, the dimension D of the piezoelectric cylinder 16 is no greater than the height H of the bore of the tube, and is preferably substantially equal thereto so as to detect all gas bubbles, if any.

For a tube having a height H of 3 mm, the ceramic cylinder 16 has a diameter of 2.5 mm and a length L of 5 mm. It is also possible to use a stratified composite 17 (FIG. 1A) in the piezoelectric cylinder. In which case, the right section of the cylinder is rectangular, e.g. having a height of 1.8 mm and a length (in a direction perpendicularly to the plane of the figure) of 4 mm. Its thickness is 2.5 mm. The axial mode excitation frequency lies in the range 200 kHz to 1500 kHz, and is preferably about 900 kHz.

After describing a simplified embodiment of the monitoring device for detecting any gas bubbles in the liquid, there follows a description with reference to FIG. 2 of a first complete embodiment of the monitoring device applied to the case of a peristaltic pump, said device serving not only to detect the presence of any bubbles in the flowing liquid, but also to detect any excess pressure of the liquid in the duct.

FIG. 2 shows a portion of the support structure 50 of the peristaltic pump, together with the outlet portion 52 of the flexible tube of the peristaltic pump. As already explained with reference to FIG. 1, the bubble detector device is constituted by two piezoelectric cylinders excited in axial mode and referenced 54 and 56 respectively, which are disposed on either side of the tube 52 and whose vibration axes YY' are substantially in alignment and orthogonal to the axis of the tube 52 in the detection zone. The two cylinders are preferably identical, and of one of the types described above. The front faces 54a and 56a of the semiconductor cylinders are fixed by any appropriate means on respective front electrodes 58 and 60. As shown in FIG. 2, the electrodes define respective cavities which preferably flare towards the tube. The active face of each piezoelectric cylinder is fixed on the cavity-closing thin wall 58a, 60a of the electrode. This thin wall, interposed between the active face of the cylinder and the duct 52 has a thickness e which is less than half the wavelength of the ultrasound waves transmitted by the piezoelectric cylinder. For the above-described ceramic cylinder, this thickness is typically equal to 0.3 mm. Also preferably, the outer face of the electrode 56 is covered in a coating of the "Teflon" type in order to provide insulation. Another solution consists in making the pieces 58 and 60 out of an electrically insulating material such as Bakelite, with the electrode and the corresponding electrical conductor being inserted in the Bakelite. The electrodes 58 and 60 are pressed against the outer face of the wall 52a of the tube 52. More precisely, the electrode 58 associated with the piezoelectric cylinder 54 is mounted in fixed manner in the support structure 50 by means of a sealing ring 62. The second electrode 64 of the cylinder 54 is fixed on its second end face and is connected to an electrical conductor 66. The receiver cylinder 56 is likewise naturally provided with a second electrode 68 fixed on its second end face and connected to an appropriate conductor 70. The set of piezoelectric cylinder 54 and 56 serves to detect the presence of any bubbles in the liquid flowing in the duct 52 by the process described with reference to FIG. 1.

In order also to detect any excess pressure of the liquid in the tube 52, and thus any deformation of the flexible wall 52a of said tube, in a preferred embodiment of the invention the electrode 60 is extended by a sleeve-forming piece 72 which surrounds the cylinder 56. The sleeve 72 is slidably mounted in a cylindrical piece 74 secured to the support structure 50 of the peristaltic pump. A resilient flexible membrane 76 provides a mechanical link between the moving electrode 60 and the support structure of the pump, thus allowing the electrode 60 to move relative to the support structure under the effect of any expansion of the tube 52. In addition, the flexible membrane tends to urge the moving assembly and thus the piezoelectric cylinder 56 against the tube 52. A cap 78 closes the cavity 80 containing the piezoelectric cylinder 56 for sealing purposes.

To detect any increase in pressure, a pressure sensor 82, preferably of the resistive type, is interposed between a rigid fixed wall 84 of the support structure and a flexible piece 86, said flexible piece being pressed against the cap 78, i.e. against the moving assembly containing the cylinder 56. In this way any deformation of the tube 52 due to excess pressure of the liquid is transmitted to the pressure sensor 82 by the moving assembly 60, 78 and the deformable piece 86. The faces of the pieces 58 and 60 are preferably coated in a material having a very low coefficient of friction, such a Teflon, as used for insulating the piezoelectric cylinders. This avoids adding interfering stresses in directions other than those of the axis XX'. The sensor then delivers an electric signal which, when processed by appropriate detector circuits, triggers an alarm signal or automatically causes operation of the pump to stop.

FIG. 3 shows a variant embodiment of the detector device of FIG. 2. In this variant, the piezoelectric sensor 54 is mounted in analogous manner to that of FIG. 2. It is therefore not described again. In contrast, the sensor 56 associated with the detector of excess pressure in the tube 52 is mounted differently. This is described below.

The active face 56a of the second sensor 56 is fixed on the piece 100 which is free relative to the housing 102 defined by the pieces 104 and 106 secured to the main support structure 108. The piece 100 and the cylinder 56 are secured to the end 110 of a strain gauge 112 operating in bending. The other end 114 of the gauge 112 is secured to the support structure 108, e.g. by being embedded therein. The strain gauge 112 performs two functions. Firstly, by bending, it detects excess pressure in the tube of the pump, which excess pressure causes the piece 100 and the sensor 56 to move and thus moves the end 110 of the sensor. Secondly, by its resilience, the gauge 112 tends to urge the piece 100 continuously against the tube of the pump.

To seal the sensor 56, the housing 102 is filled with a gel which, once set, is of a consistency suitable for enabling it to remain within the housing 102, but which gives rise to no friction or other constraints when the piece 100 moves under the effect of excess pressure in the tube of the pump.

To further improve the accuracy with which excess pressure in the tube is detected, two pieces 120 and 122 disposed at a right-angle relative to the axis of the sensors 54 and 56 are secured to the cassette. These pieces which have faces 120a and 122a in the form of portions of a cylindrical surface, prevent the tube deforming in the orthogonal direction ZZ', thus concentrating deformation of the tube in the direction "X—X" of the axes of the sensors, and thus in the displacement direction of the end 110 of the strain gauge 112.

We claim:

1. A monitoring device for monitoring the flow of a liquid in a tubular duct, comprising:

a support structure of a peristaltic pump including a deformable tube having an outlet portion forming the tubular duct;

a first piezoelectric cylinder whose vibration axis is substantially orthogonal to said duct in a detection zone and which is mounted on said support structure to be disposed on a first side of said duct, said first cylinder being fixed relative to said support structure;

means for exciting said first piezoelectric cylinder in an axial mode at a predetermined frequency F lying in the range 100 kHz to 1500 kHz, in order to transmit ultrasound waves;

a second piezoelectric cylinder whose axis coincides substantially with that of the first cylinder and that is disposed on a second side of said duct, whereby said second cylinder receives said ultrasound waves after they have passed through said duct; said second piezoelectric cylinder being secured to a moving support moveable in translation relative to said support structure along the direction of the axis of the cylinder;

a resilient means interposed between said support structure and said moving support tending to press said second cylinder against the wall of the duct, a displacement detection means for detecting displacement of said moving support relative to the support structure under the effect of deformation of said duct because of excess pressure of the liquid flowing along said duct;

means for picking up an electric signal representative of the amplitude of axial vibration of said second cylinder; and processor means for processing said electric signal to deduce therefrom the presence of a gas bubble in the liquid flowing in said duct through the detection zone.

2. A device according to claim 1, characterized in that the displacement detection means comprise a pressure sensor interposed between the support structure and one end of said moving support.

3. A device according to claim 2, characterized in that said pressure sensor is a resistive sensor.

4. A device according to claim 1, characterized in that said displacement detection means includes a strain gauge operating in bending having one end secured to said moving support and having its other end secured to the support structure, whereby said strain gauge tends to press said moving support against the tubular duct of said pump, and detects displacements of said support to detect any excess pressure in the tubular duct.

5. A device according to claim 4, characterized in that said support and said second piezoelectric cylinder are mounted in a housing of the support structure, said housing being filled with a gel.

6. A device according to claim 1, characterized in that said two cylinders are identical.

7. A device according to claim 1, characterized in that, in a plane perpendicular to an axis of the duct, a dimension of a transmitter/receiver face of at least one of the piezoelectric cylinder is no greater than a height of a bore of said duct.

8. A device according to claim 1, characterized in that said cylinders are made of a ceramic optimal for said predetermined frequency.

9. A device according to claim 1, characterized in that said cylinders are made of a stratified composite material optimal for said predetermined frequency.

10. A device according to claim 1, characterized in that at least one of said piezoelectric cylinders includes a coating.

11. A device according to claim 10, characterized in that said coating includes Teflon.

* * * * *